United States Patent [19]

Noguchi

[11] Patent Number: 4,870,487
[45] Date of Patent: Sep. 26, 1989

[54] LIGHT SOURCE DEVICE FOR AN ENDOSCOPE WHICH MAINTAINS A CONSTANT MINIMUM-DC CURRENT

[75] Inventor: Toshiaki Noguchi, Tachikawa, Japan

[73] Assignee: Olympus Optical Co., Ltd., Tokyo, Japan

[21] Appl. No.: 245,885

[22] Filed: Sep. 15, 1988

Related U.S. Application Data

[62] Division of Ser. No. 119,604, Nov. 12, 1987, Pat. No. 4,800,424.

[30] Foreign Application Priority Data

Nov. 13, 1986 [JP] Japan .................................. 61-270461
Apr. 27, 1987 [JP] Japan .................................. 62-85528

[51] Int. Cl.⁴ .............................................. H04N 7/18
[52] U.S. Cl. .......................................... 358/98; 128/6
[58] Field of Search ................... 358/98, 211, 42, 228, 358/901, 213.18; 128/4, 6

[56] References Cited

U.S. PATENT DOCUMENTS

| 4,423,436 | 12/1983 | Kimura ................................. 358/98 |
| 4,546,379 | 10/1985 | Sarofeen et al. .................. 358/98 X |
| 4,602,281 | 7/1986 | Nagasaki et al. ..................... 358/98 |
| 4,769,693 | 9/1988 | Kato ....................................... 358/98 |

*Primary Examiner*—James J. Groody
*Assistant Examiner*—Victor R. Kostak
*Attorney, Agent, or Firm*—Armstrong, Nikaido, Marmelstein, Kubovcik & Murray

[57] ABSTRACT

A white light of a lamp, which can flash, is passed through a rotary filter fitted with a plurality of color filters to output field sequential type colored light. An output signal of a color filter detecting device, detecting the timing when the color filters are interposed in a light path, is used to produce trigger signals having different delay amounts. The light emitting timing of the lamp is delayed relatively from the time when the color filters are interposed in the light path to control the emitted light amounts of the colored light.

8 Claims, 8 Drawing Sheets

(a) STANDARD CLOCK
(b) APERTURE TIME OF FILTER
(c) TIMING SIG. OF ILLUMINATION
(d) SHAPE OF ILLUMINATION
(e) OUTPUT LIGHT
(f) SHAPE OF FLASH
(g) OUTPUT LIGHT

LIGHT SOURCE DEVICE FOR AN ENDOSCOPE WHICH MAINTAINS A CONSTANT MINIMUM-DC CURRENT

This is a divisional application of U.S. Pat. No. 4,800,424.

BACKGROUND OF THE INVENTION

Field of the Invention and Related Art Statement

This invention relates to an endoscope light source apparatus provided with a means of controlling an illuminating light amount to an object to be imaged.

In an endoscopic observation, an exclusive light source apparatus is used so that an illuminating light from the light source apparatus may be radiated onto an object to be imaged from a tip of an endoscope through light guide fibers within the endoscope. In order to adjust the illuminating light amount in response to the brightness (reflection factor) of the object to be imaged, a diaphragm blade is provided between a connector with the endoscope and a lamp within the light source apparatus. A slitted plate or honeycomb plate provided rotatably with the axis intersecting at right angles with a light path as a center is used for such diaphragm blade. That is to say, by electrically or mechanically rotating this a diaphragm blade, the light intercepting rate can be varied to adjust the light amount incident upon the light guide. A related art example using a honeycomb diaphragm is mentioned in a Japanese patent application No. 173832/ 1984.

Figures 1, 2:
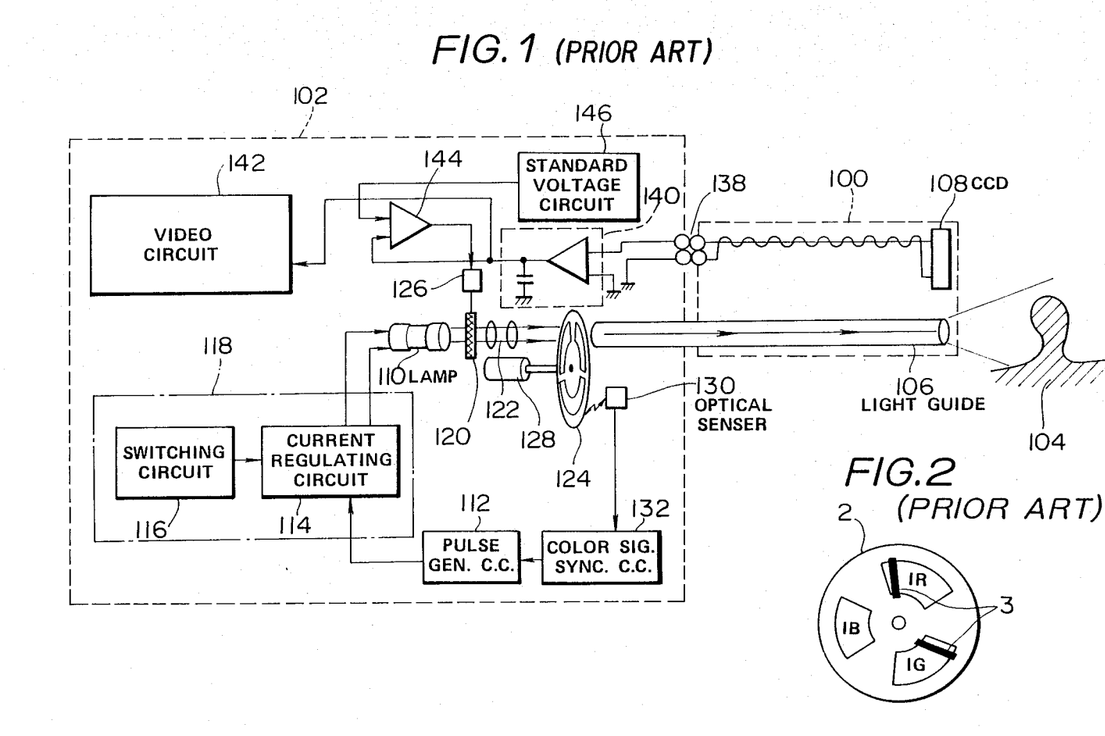
FIG. 1 is a block diagram of a light source apparatus of the first prior art example.
FIG. 2 is a view showing a rotary filter used in the second prior art example.

The endoscope light source apparatus of the above mentioned ralated art example shall be explained with reference to FIG. 1. Here, a so-called electronscope in which a solid state imagining device is built within the tip part of an insertable part to image an object shall be explained. A light source apparatus 102 is connected to an electronscope 100. The electronscope 100 is provided with a light guide 106 consisting of an optical fiber bundle leading an illuminating light radiated from the light source apparatus to the tip of the insertable part to illuminate an object 104 and a charge coupled device (CCD) 108 as a solid state imaging device built within the tip part.

The light source apparatus 102 is provided with a light source such as, for example, a lamp (xenone lamp) 110. The lamp 110 is regulated to be of a constant current so that, when an output signal of a pulse generating circuit 112 is input into a current regulating circuit 114, a flash will be emitted as synchronized with the signal. A switching circuit 116 is connected to the current regulating circuit 114 to form a light source lighting circuit 118.

The light emitted from the lamp 110 is incident upon the light guide 106 of the electronscope 100 through a diaphragm blade 120, optical lens system 122 and rotary filter 124. The diaphragm blade 120 is rotated by a driving device 126 and consists of a slitted plate or honeycomb plate variable in the inclination with the light path. The rotary filter 124 is rotated by a motor 128 and colors the illuminating light in red (R), green (G) and blue (B) in turn. There is a light intercepting period between the exposure periods of the respective color components. An optical sensor 130, detecting the exposure periods of the respective color components of the rotary filter 124, is provided. When the exposure periods of the respective color components end, a pulse will be output from the optical sensor 130 and will be fed to a color signal synchronizing circuit 132. After a predetermined period (corresponding to the light intercepting period) from this synchronizing pulse, only for a fixed period (corresponding to the exposure period), the color signal synchronizing circuit 132 feeds a color synchronizing signal to the pulse generating circuit 112 so that the lamp 110 may be synchronized with the rotation of the rotary filter 124 and may emit a light only in the exposure periods of the respective colors.

The output signal of the CCD 108 is fed to the light source device 102 side through a signal line and connector 138 within the electronscope 100 and is input into a signal processing circuit 140 making an amplification, clamping and various corrections. The output of the signal processing circuit 140 is fed to a video circuit 142 and a picture image is output in a displaying part (not illustrated). The output of the signal processing circuit 140 is input also into a differential amplifier 144. The standard signal of the differential amplifier is given by a standard voltage circuit 146. The output of the differential amplifier 144 regulates the diaphragm driving device 126.

An integrator is also provided within the signal processing circuit so that the illuminating light amount may be detected. The difference between this light amount value and the standard signal is operated by the differential amplifier 144. In response to this result, the diaphragm driving device 126 is regulated. Thereby, the diaphragm blade 120 will be inclined in the direction of intercepting the light in case the illuminating light is too bright and will be inclined in the direction of opening the light path in case the illuminating light is too dark. This automatic light adjusting operation is the same not only in an electronscope but also in an ordinary fiberscope.

In a conventional light source apparatus for endoscopes, the diaphragm blade is exclusively for adjusting the light, the driving mechanism is for rotating the diaphragm blade and their control circuit are separately required. Therefore, defects have caused the number of the component parts to increase and has caused the light source apparatus to become large, complicated and costly.

Now, in an electronic endoscope apparatus using a field sequential system, in order to improve the color reproductivity of an endoscope picture image, it is necessary to adjust the color balance (white balance) of R, G and B in advance. In the case of using, for example, as a prior art example, the rotary filter 2 provided with respective R, G and B color transmitting filters 1R, 1G and 1B as shown in FIG. 2 for a light source emitting a continuous light, there is used a method of adjusting the aperture ratio of the respective R, G and B color transmitting filters 1R, 1G and 1B by using the light intercepting member 3. Even if the aperture rates of the respective R, G and B color transmitting filters 1R, 1G and 1B are set in advance, depending on the dispersion of the imaging device or the like, it can not be said that the best state can always be held. In such a case, a light intercepting member is further added to the aperture surface of the filter set in advance.

In this prior art example, even if the aperture rates of the respective color transmitting filters are set in advance, due to the dispersion of the imaging device or the like, the aperture rates of the respective color filters must be readjusted by using a light intercepting member. In such a case, defects occur where no accurate color balance adjustment can be made, a light intercepting member is required and a large amount of time is needed for the adjustment.

Figures 3A, 3B:
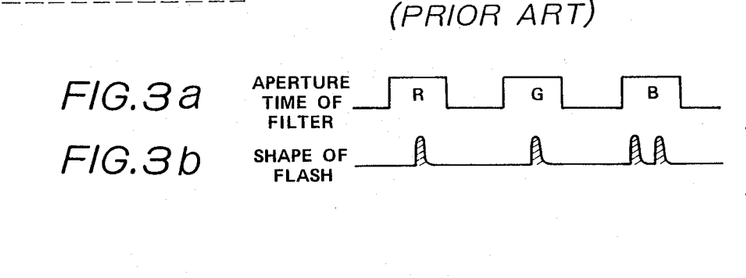
FIG. 3 shows operation explaining diagrams of the third prior art example.

When a flash light source is used (which shall be referred to as a strobo lamp hereinafter), and when the energy fed to the strobo lamp is made variable, the emitted light amount can be adjusted. Therefore, when proper energy is fed to the strobo lamp to emit a light within the aperture time of the respective R, G and B color filters as shown in FIG. 3a, the R, G and B color balance can be adjusted the same as in the above mentioned example.

In order to make the fed energy variable, there is adopted a method wherein the number of times of the strobo light emission is made variable during the aperture time of the respective color filters.

In the method wherein the number of times of the light emission of the strobo lamp during the aperture periods of the respective color filters is thus controlled, it is necessary to expand the control range by increasing the number of times of the light emission of the strobo lamp which therefore causes a defect in that the life of the strobo lamp is extremely reduced.

Also, as disclosed in a Japanese patent laid open No. 205884/1984 (or U.S. Pat. No. 4,532,918), a multi-strobo-type lamp is used such as the lamp is turned on and off repeatedly. This type of lamp requires a high lighting voltage to be supplied each time it is turned on after a stop. In consequence, noise is liable to be generated in the circuit and the circuit is inevitably rendered complicated in construction.

Objects and Summary of the Invention:

To provide an improved endoscope light source device which is to suppress generation of noise when it is started and which does not require the circuit to become complicated.

In contrast to the multi-strobo-type lamp used in the art of U.S. Pat. No. 4,532,918, the D.C. lighting type lamp used in the present invention can be turned on and off simply by increasing or decreasing the level of the electric current. Namely, it is not necessary to repeatedly turn on and off the high lighting voltage and the generation of noise is suppressed accordingly. The lamp of the type used in the art of U.S. Pat. No. 4,532,918 cannot be used as the light source of the fiber scope, whereas the lamp of the type used in the present invention can be used as a light source for a fiber scope because it can be continously maintained in an on state.

BRIEF DESCRIPTION OF THE DRAWINGS

FIGS. 8 to 11 relate to the third embodiment of the present invention.

DETAILED DESCRIPTION OF PREFERRED EMBODIMENTS

Figure 4:
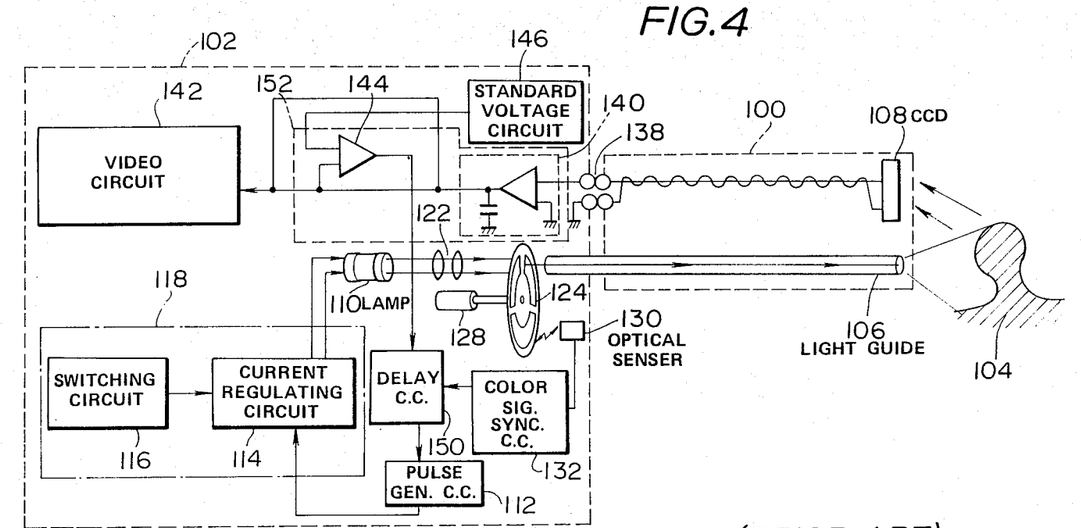
FIG. 4 is a schematic diagram of a light source apparatus of the first embodiment of the present invention.

FIG. 4 is a schematic diagram of the first embodiment. The same reference numerals are attached to the same parts as in the prior art example in FIG. 1. The difference from the prior art example is that a delaying circuit 150 is provided between the differential amplifier 144 and pulse generating circuit 112 without providing a diaphragm blade and diaphragm driving device. For the convenience of explanation, here the signal processing circuit 140 and differential amplifier 144 are combined to be a light adjusting signal generating circuit 152.

Figure 5:
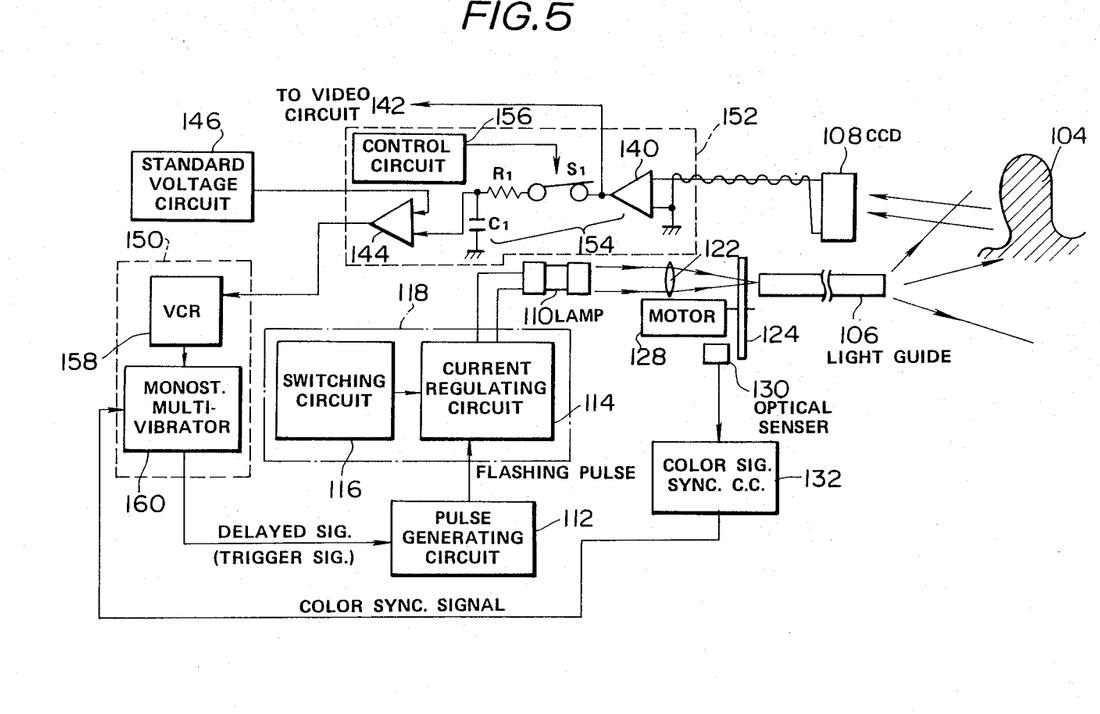
FIG. 5 is a block diagram showing a detailed formation of the first embodiment.

FIG. 5 shows the details of the delaying circuit 150 and light adjusting signal generating circuit 152 of the first embodiment. The output of the CCD 108 is input into the signal processing circuit 140. The output of the signal processing circuit 140 is fed to the integrator 154 consisting of a switch S1, resistance R1 and capacitor C1. The switch S1 is controlled to open and close by the control circuit 156. The output of the integrator 154 is fed to the differential amplifier 144.

The delaying circuit 150 comprises a voltage controlling resistor (VCR) 158 and a monostable multivibrator 160. The VCR 158 varies the resistance value with the applied voltage. The output of the differential amplifier 144 is applied to the VCR 158. The VCR 158 becomes a resistance determining the time constant of the monostable multivibrator 160. The output of the color signal synchronizing circuit 132 is input into the monostable multivibrator 160 and the output of the momostable multivibrator 160 is fed to the pulse generating circuit 112.

Figure 6A:
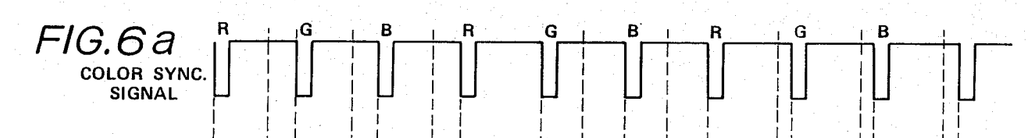
FIGS. 6a–6f are timing charts showing the operation of the first embodiment.
Figure 6B:
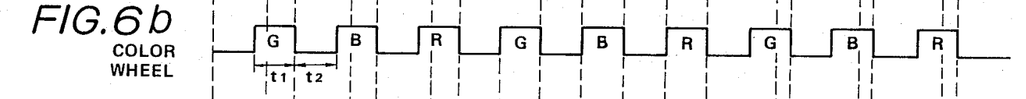

The operation of the first embodiment shall be explained in the following with reference to the timing charts shown in FIGS. 6a to 6f. With the rotation of the rotary filter 124, a color synchronizing signal such as is shown in FIG. 6a will be output from the color signal synchronizing circuit 132. The filtering manner by the rotary filter 124 is shown in FIG. 6b. The exposure period is represented by t1 and the light intercepting period is represented by t2. That is to say, when the exposure of the respective colors ends, a color synchronizing signal will be output. The color synchronizing signal triggers the monostable multivibrator 160 but, in this embodiment, the time constant of the monostable multivibrator 160 is determined by the VCR 158 varying the resistance value with the output of the light adjusting signal generating circuit. After the monostable multivibrator 160 is triggered and the time of the time constant passes, the output rises to output a pulse of a fixed width. The resistance value of the VCR 158 will increase when the light adjusting signal increases but will decrease when it decreases. Therefore, the delayed time of the delaying circuit 150 will also increase when the light adjusting signal increases but will decrease when it decreases.

Figure 6C:
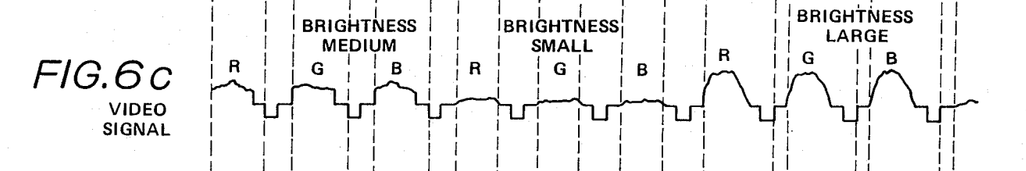
Figure 6D:
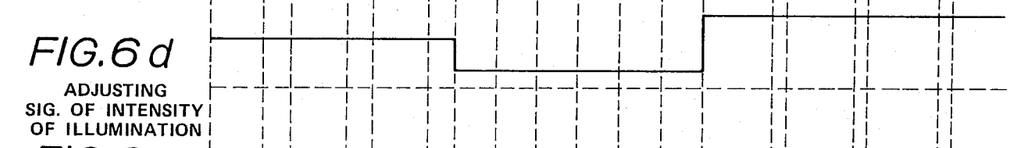

It is assumed that the brightness of an object to be imaged varies from being medium to being small and from being small to being large. The output video signal of the CCD 108 then is shown in FIG. 6c. This video signal is integrated by the integrator 154 and the integrated value per frame is held by the capacitor C1. This integrated output is shown in FIG. 6d. The integrated output is fed to one input terminal of the differential amplifier 144. The standard signal fed to the other input terminal of the differential amplifier 144 is shown by the broken line in the same diagram. The difference between the standard signal and integrated signal is applied as a light adjusting signal to the VCR 158 as a control voltage. That is to say, the larger the brightness of the object to be imaged, the larger the delayed time of the delaying circuit 150.

Figure 6E:
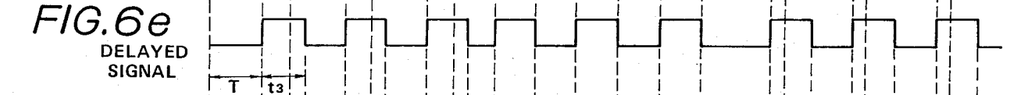
Figure 6F:
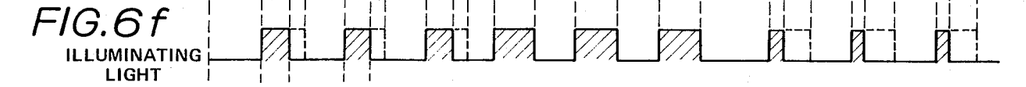

Thus, the delayed signal delayed by T in response to the brightness of the object from the color synchronizing signal (in FIG. 6a) is fed to the pulse generating circuit 112 from the monostable multivibrator 160. The delayed signal is shown in FIG. 6e. During the period t3 in which this delayed signal is being generated, the pulse generating circuit 112 will flash the lamp 110 through the light source lighting device 118. Here, when the brightness of the object is medium or large, before the flashing period t3 ends, the light intercepting period t2 of the rotary filter will start and therefore the later half of the emitted light will be intercepted as shown in FIG. 6f. Therefore, the emitted light amount of the lamp 110 incident upon the light guide 106 will reduce to be smaller then when the brightness of the object is small. Therefore, even if no diaphragm is used, the light will be able to be automatically adjusted.

The following relations are necessary among the flashing period t3, exposure period t1 and light intercepting period t2.

$$t3 < t2 \quad (1)$$

$$t1 + t2 > T + t3 \quad (2)$$

As explained above, according to this embodiment, there can be realized an endoscope light source apparatus wherein, by delaying the flashing starting timing of the lamp to be later than the exposure starting timing of the rotary filter in response to the light adjusting signal, the light can be automatically adjusted with a simple formation without using the diaphragm blade.

Since as the light adjusting signal is determined on the basis of the difference between the integrated output and standard signal, the light can be adjusted to be of any desired brightness by varying the voltage of the standard signal.

Figure 7:
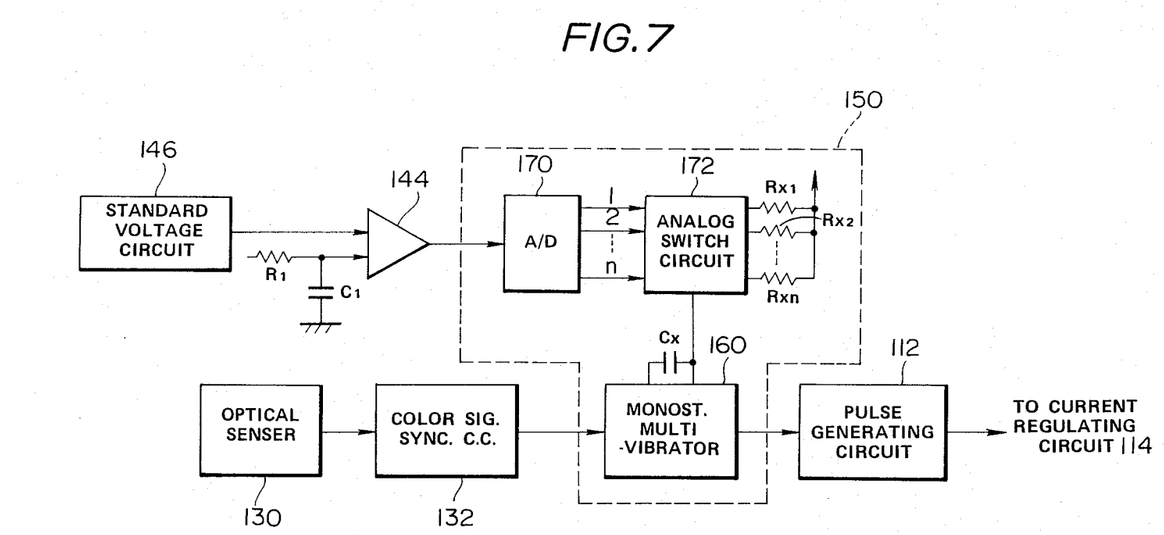
FIG. 7 is a block diagram of an essential part of the second embodiment of the present invention.

The second embodiment of this invention shall be explained in the following. FIG. 7 is a block diagram of an essential part of the second embodiment. The second embodiment is different from the first embodiment only in the formation of the delaying circuit 150 but is the same otherwise. That is to say, the output of the differential amplifier 144 is input into an A/D converter 170. The A/D converter 170 converts the A/D by a sampling pulse from the control circuit 156, makes only the output of any of 1 to n effective and conducts only the corresponding analogue switch in the analogue switch circuit 172. Thereby, any one of external resistances $R \times 1$ to $R \times n$ is selected and is connected to the time constant circuit of the monostable multivibrator 160 and the time constant is determined by Rx and Cx. Therefore, also in the second embodiment, as the delaying circuit 150 feeds a delayed signal delayed from the color synchronizing signal to the pulse generating circuit in response to the light adjusting signal, the flashing start of the lamp 110 will be delayed and the light will be automatically adjusted.

This invention is not limited to the above described embodiment and can be variously modified. The lamp 110 may be any flashable lamps such as a direct current arc discharge lamp and strobo lamp. This flashing means that the light amount can be increased or decreased by the increase or decrease of the lamp current. The light need not always be extingushed during the light intercepting period. Further, the delayed time of the delaying circuit 150 can be manually adjusted not by the light adjusting signal and the light may be adjusted manually not automatically. The light source for electronscopes has been explained but can be applied also to a light source for fiberscopes wherein a television camera is fitted to an eyepiece part.

As explained above, according to the first and second embodiments, there can be realized an endoscope light source apparatus of a simple formation requiring neither mechanical diaphragm blade nor diaphragm driving device. Thus, the number of the component parts is reduced, the apparatus can be made small and the price can be made low.

Figure 8:
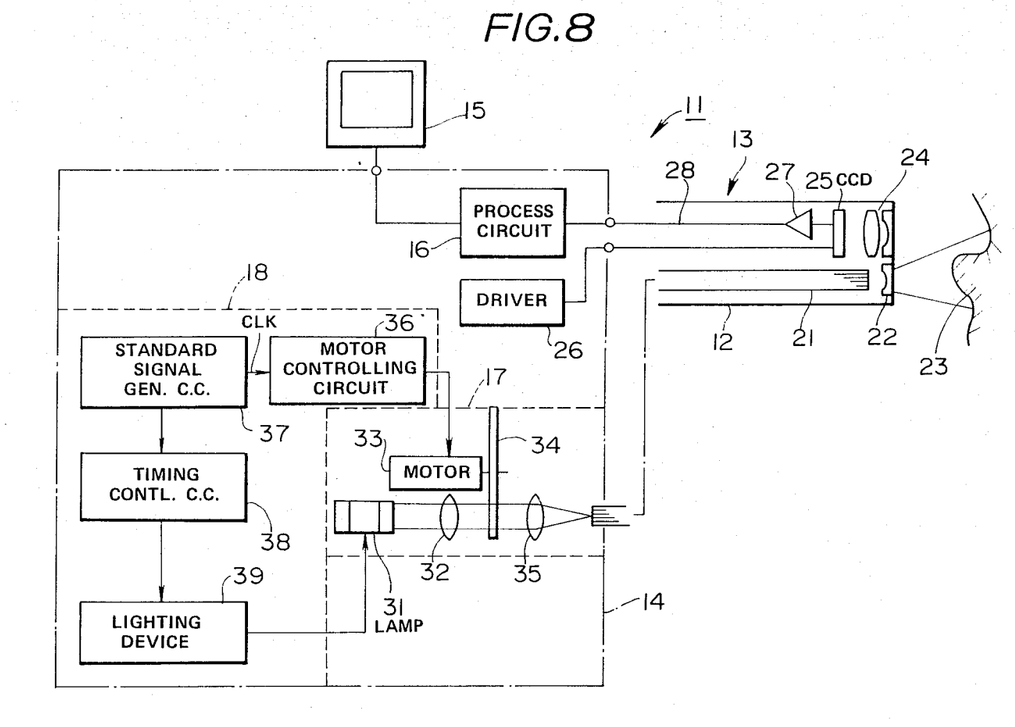
FIG. 8 is a formation diagram of an electronic endoscope apparatus provided with the third embodiment.

As shown in FIG. 8, an electronic endoscope apparatus 11 provided with the third embodiment comprises an electronic endoscope 13 having an insertable part 12 elongated so as to be insertable into a body cavity or the like, a video processor 14 into which the signal imaged by this electronic endoscope 13 is to be input and a color monitor 15 color-displaying the video signal processed by this video processor 14.

A (video) processing circuit 16 processing the signal, a light source apparatus 17 feeding an illuminating light and a color balance adjusting part 18 are built within the above mentioned video processor 14.

A light guide 21 transmitting the illuminating light is inserted through the insertable part 12 of the above mentioned electronic endoscope so that the illuminating light fed from the light source part 17 to the entrance end may be transmitted to be emitted from the exit end and an object 23 to be imaged may be illuminated by the illuminating light expanded through a light distributing lens 22.

The illuminated object 23 is imaged on the imaging surface of a CCD 25 by an objective lens 24. When a driving signal output from a driver 26 is applied, the CCD 25 will output a photoelectrically converted signal. This signal is amplified by an amplifier 27 and is then input into the processing circuit 16 within the video processor 14 through a signal cable 28. The signal is processed by this processing circuit 16 to produce an NTSC compound video signal which is color-displayed by the color monitor 15.

The above mentioned light source apparatus 17 within the above mentioned video processor 14 is of a field sequential type. The white light of a light source lamp 31 is made a parallel beam by a collimator lens 32. A rotary filter 34 rotated and driven by a motor 33 is interposed on a light path made by this parallel beam. The light passed through this rotary filter 34 is further condensed by a condenser lens 35 and is radiated onto the entrance end surface of the light guide 21.

In the above mentioned rotary filter 34, three sector apertures are formed in a disc frame and color transmitting filters 34R, 34G and 34B transmitting respectively red, green and blue colors are fitted in the respective apertures. When the rotary filter 34 is rotated and driven, these color (transmitting) filters 34R, 34G and 34B will be interposed and retreated sequentially in the course of the light path. The time when the respective color filters 34R, 34G and 34B are interposed on the light path is mentioned as the aperture time of the filter.

When the above mentioned color filters 34R, 34G and 34B are interposed sequentially on the light path, the lights, that is, the red, green and blue illuminating lights having passed through these color filters 34R, 34G and 34B, will be fed sequentially onto the entrance end surface of the light guide 21. Therefore, the object 23 is illuminated sequentially by the lights of wavelengths of red, green and blue. The signal imaged under this field sequential illuminating state is input into the processing circuit 16.

Now, the motor 33, to make the above mentioned field sequential illumination, is controlled by the rotation controlling signal output from a motor controlling circuit 36 so that its rotating speed may be constant. A standard clock signal CLK output from a standard signal generating circuit 37 is input into this motor controlling circuit 36 to produce a rotation controlling signal synchronized with this standard clock signal CLK. As the motor 33 is synchronized with the standard clock signal CLK and is controlled to be at a constant speed, as shown in FIG. 9b, the aperture time when the respective color filters 34R, 34G and 34B are interposed on the light path will be also synchronized with the standard clock signal CLK in FIG. 9a. The above mentioned standard signal generating circuit 37 outputs the standard clock signal CLK also to a timing controlling circuit 38. This timing controlling circuit 38 outputs a light emitting timing signal such as is shown in FIG. 9c to a lighting device 39 lighting the light source lamp 31 to control the light emitting time of the light source lamp 31.

By the above mentioned light emitting timing signal, the light emitting time of the light source lamp 31 is controlled and, by the relation between this light emitting time and the filter aperture time, the fed light amount (emitted light amount) fed actually to the light guide 21 is variably controlled and the color balance is adjusted.

That is to say, when the light emitting timing signal is made to coincide with the aperture time of the filter, the timing when the color filters 34R, 34G and 34B are interposed on the light path and the timing when the light source lamp 31 emits the light will coincide with each other and therefore the emitted light amount to the light guide 21 will become large. On the other hand, when the light emitting timing time is displaced as shown in FIG. 9c from this filter aperture time, as shown in FIG. 9d, the light emitting time will be displaced and the light emitting waveform will be also displaced. Only for the light emitting period overlapping the aperture time, the output light will be fed actually to the light guide 21. This output light period is shown in FIG. 9c.

Thus, the timing of outputting the light emitting timing signal is controlled and the emitted light amount to the light guide is variably controlled to adjust the color balance.

The operation of the embodiment in FIG. 7 shall be explained in the following with reference to FIG. 9.

As in FIG. 9a, a standard clock signal is oscillated by the standard signal generating circuit 37 and is input into the motor controlling circuit 36 and timing controlling circuit 38. The rotary filter 34 fitted to the motor 33 is controlled to rotate at a constant speed by the motor controlling circuit 36 by the signal synchronized with the standard clock signal. Therefore, as in FIG. 9b, the aperture time and timing of the respective color filters synchronized with the standard clock signal are determined. Here, T1 represents the aperture time of R(red), T2 represents the aperture time of G(green) and T3 represents the aperture time of B(blue). As in FIG. 9c, a light emitting timing signal synchronized with the standard clock signal, the same as in the above mentioned aperture time, is output from the timing controlling circuit 38. Signals delayed by the time t1 for the rise of the aperture time of R, by the time t2 for the rise of the aperture time of G and by the time t3 for the rise of the aperture time of B are shown to be output. The signal shown in FIG. 9c is input into a lighting device 39 for lighting and controlling the light source lamp 31. The light source lamp 31 emits a light as synchronized with the above mentioned light emitting timing signal. FIGS. 9d and 9e are of examples of controlling the current fed to a continuously lighted lamp such as a direct current arc discharge lamp. The output light output on a low level shows a residual light. In this example, the current of the lamp is controlled as synchronized with the light emitting timing signal to control the emitted light.

Figure 9:
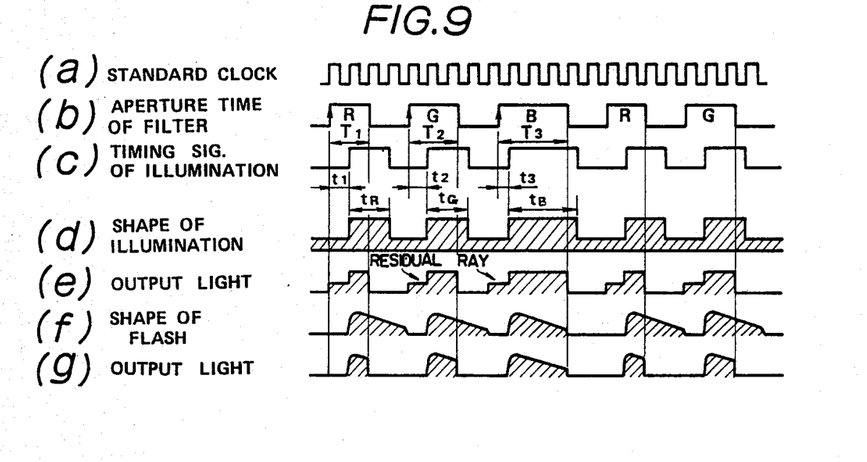
FIGS. 9(a)–(g) are an operation explaining view of the first embodiment.

As shown in FIG. 9, as the light source emits a light (the light amount increases) as delayed by the time t1 (or t2 or t3) for the timing of the filter aperture time T1 (or T2 or T3), the light emission will continue to the light intercepting period of the rotary filter 34. That is to say, if the filter aperture time and the light emitting timing are simultaneous without delay, the emitted light will be all emitted during the period of tR (or tG or tB) and the light amount will be 100% output light but, if a delayed time of t1 (or t2 or t3) is provided, the emitted light will be delayed by the time of t1(or t2 or t3) and the light will become darker by the emitted light for the time of t1 (or t2 or t3) than in the state of 100%. In the present application, the color balance is adjusted by utilizing this point. When the above mentioned time t1, t2 and t3 are independently freely controlled, the amount of the emitted light colored in the respective colors will be varied and therefore the color balance can be adjusted very simply and accurately. For example, after the time t1, t2 and t3 are set to be optimum, if the time t1, t2 and t3 are varied at the same ratio so as to follow the brightness level of the video signal, the light can be adjusted.

FIGS. 9f and 9g are of examples of using a strobo lamp. The difference in this case is the difference of the light emitting system of the light source lamp 31.

The above mentioned direct current arc discharge lamp has a characteristic that it can not be lighted just after it is extinguished. Therefore, the lamp current is increased or decreased to emit a light as synchronized with the light emitting timing. In such a case, a residual light shown in FIG. 9e will be generated. On the other hand, in the strobo lamp, there are advantages that the light can be perfectly set on and off, can be therefore continuously emitted within a short time, the flashing time is also short, therefore the imaging time is short and a sharper image is obtained.

Figure 10:
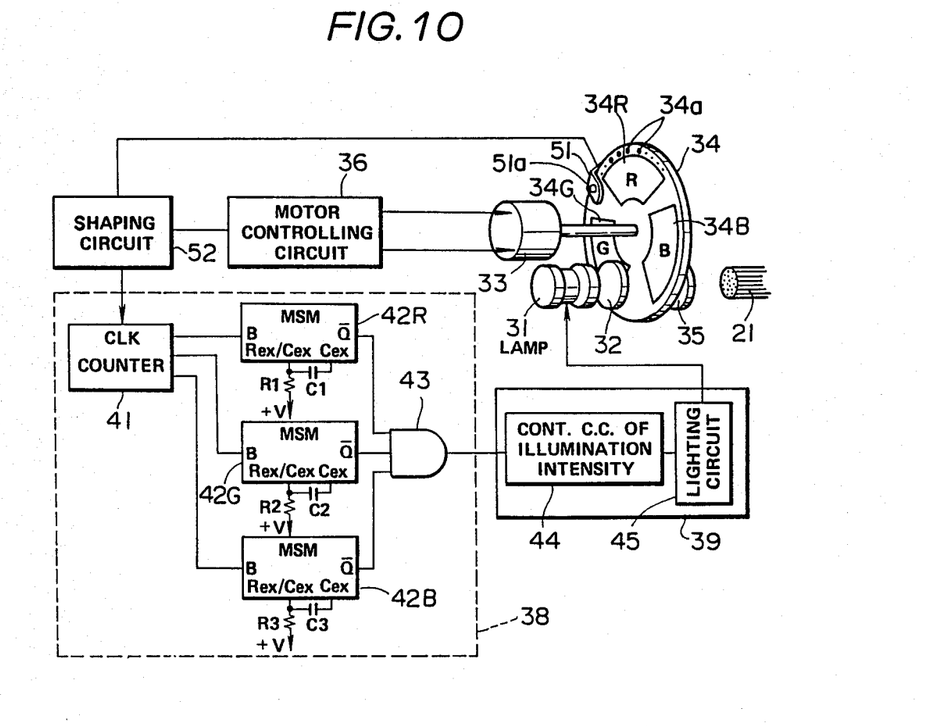
FIG. 10 is a formation diagram of the fourth embodiment of the present invention.
Figure 11:
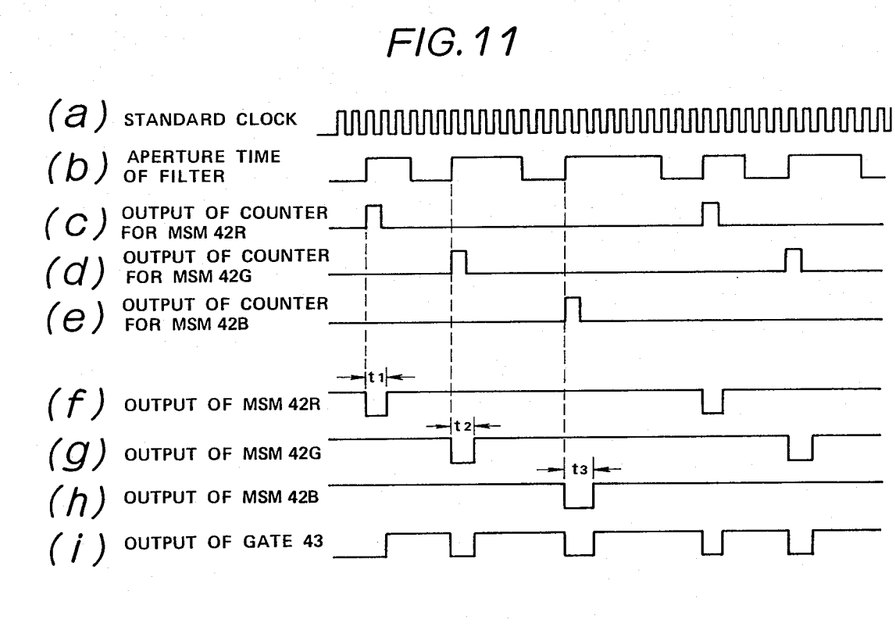
Figure 12:
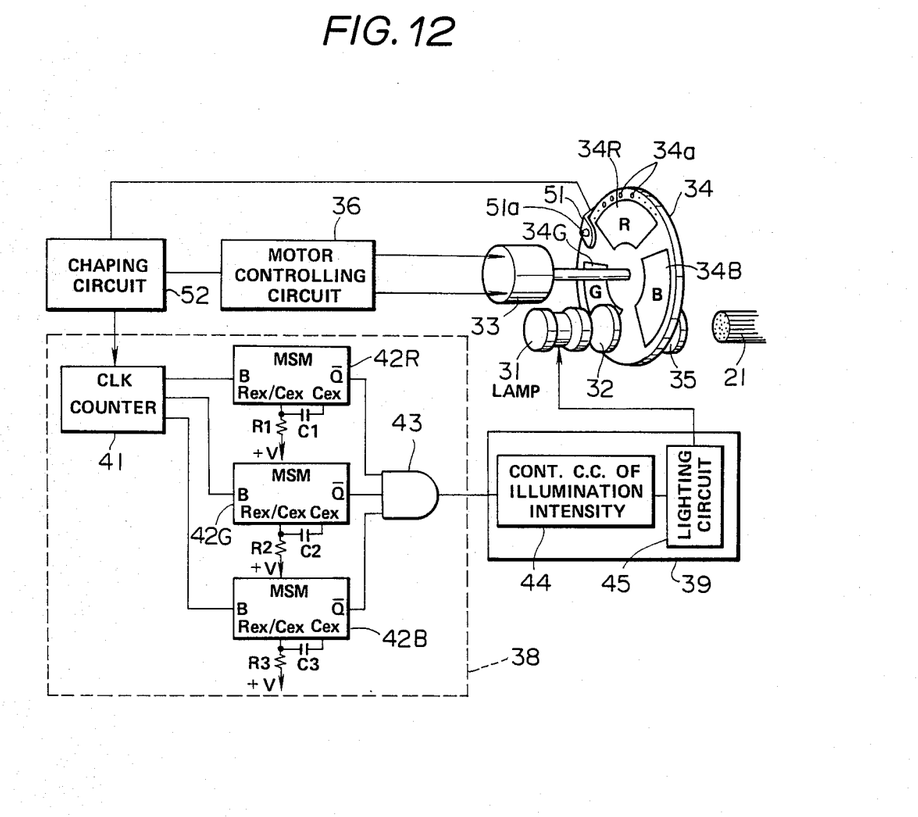

FIG. 10 shows a concrete formation of the fourth embodiment.

In this embodiment a sensor 51 is for sensing the rotating speed of the rotary filter 34 and the waveform shaping circuit 52 is for shaping the waveform of a signal output from this sensor 51 and inputting the signal into the counter 41.

The above mentioned sensor 51 comprises a light emitting device and light receiving device 51a arranged to hold a filter frame, for example, of the rotary filter 34 so that a light pulse, in case the light receiving device 51a receives the light of the light emitting device through holes 34a provided at regular intervals in the peripheral direction of the filter frame, may be photoelectrically converted and led to the waveform shaping circuit 52.

The motor 33 fitted with the rotary filter 34 rotates at a constant speed by the motor controlling circuit 36. The sensor 51, sensing the rotating speed of the rotary filter 34, is provided in a proper position on the periphery of the rotary filter 34 so that the signal obtained from the sensor 51 may have the waveform shaped by the waveform shaping circuit 52. This signal operates as a standard clock signal as in FIG. 9a.

The operation of this embodiment shall be explained in the following.

A standard clock signal obtained by the above mentioned waveform shaping circuit 52 is counted by the counter 41, is synchronized with the aperture time of the filter and is fed to the respective delaying circuits 42R, 42G and 42B. Therefore, a light emitting timing signal, having the delayed time t1, t2 and t3 set by the constants Ri and Ci provided in the respective delaying circuits, is fed to the lighting device 39 as in FIG. 9c. Therefore, the emitted light amount passing through the respective color filters can be freely adjusted and therefore the color balance can be adjusted.

In this embodiment, even when the speed of the rotary filter 34 is unstable, as the rotating speed is always sensed and the light emitting timing signal is output, the color balance can be adjusted more accurately.

A means of detecting the positions of the respective color filters interposed on the light path may be provided and the light may be extinguished except at the aperture time.

The above mentioned respective embodiments have a feature that the colors can be balanced irrespective of the kind of the light source lamp.

The emitted light amount can be also controlled by emitting, as pulses, the emitted light amounts of the R, G and B lamps.

As described above, according to the fourth embodiment, as the lighting of the light source lamp is controlled through the delaying means synchronized with the time when the respective color filters of the rotary filter are interposed, the color balance can be adjusted at a high precision with a simple formation.

What is claimed is:

1. A light source device for supplying illuminating light to an endoscope comprising:
    a short-arc lamp emitting light in response to a supply of a D.C. current;
    lighting circuit means for supplying a D.C. base current of a low level to said short-arc lamp and for supplying a pulse current of a high level at a suitable period to turn on said short-arc lamp; and
    shutter means, disposed in a path of light of the illuminating light emitted from said short-arc lamp, said shutter means for opening and closing at a period which is substantially the same as the period of turning on of said short-arc lamp.

2. A light source device according to claim 1, wherein said lighting circuit means is for supplying at least said D.C. base current in the period in which said shutter means is closed.

3. A light source device according to claims 1 or 2, wherein said lighting circuit means is for supplying said D.C. base current regardless of a state of said shutter means.

4. A light source device according to any one of claims 1 or 2, wherein said shutter means includes a rotary filter having a light-shielding disk frame having a plurality of sector openings arranged in the circumferential direction and color transmitting filters on the plurality of sector openings, and a motor for rotatingly driving said rotary filter to bring said color transmission filters successively into the path of the illuminating light.

5. A light source device according to claim 4, wherein said color transmission filters transmit lights of wavelengths corresponding to red, green and blue colors.

6. A light source device for supplying illuminating light to an endoscope comprising:
    a short-arc lamp emitting light in response to a supply of a D.C. current;
    lighting circuit means for supplying a D.C. base current of a low level to said short-arc lamp and for supplying a pulse current of a high level at a suitable period to turn on said short-arc lamp; and
    shutter means, disposed in a path of light of the illuminating light emitted from said short-arc lamp, said shutter means for opening and closing at a period which is substantially the same as the period of turning on of said short-arc lamp, said shutter means including a rotary filter having a light-shielding disk frame having a plurality of sector openings arranged in the circumferential direction and color transmitting filters on the plurality of sector openings, and a motor for rotatingly driving said rotary filter to bring said color transmission filters successively into the path of the illuminating light, wherein said lighting circuit supplying said D.C. base current regardless of a state of said shutter means.

7. A light source device for supplying illuminating light to an endoscope comprising:
    a short-arc lamp emitting light in response to a supply of a D.C. current;
    lighting circuit means for supplying a D.C. base current of a low level to said short-arc lamp and for supplying a pulse current of a high level at a suitable period to turn on said short-arc lamp; and
    shutter means, disposed in a path of light of the illuminating light emitted from said short-arc lamp, said shutter means for opening and closing at a period which is substantially the same as the period of turning on of said short-arc lamp, said shutter means including a rotary filter having a light-shielding disk frame having a plurality of sector openings arranged in the circumferential direction and color transmitting filters on the plurality of sector openings, and a motor for rotatingly driving said rotary filter to bring said color transmission filters successively into the path of the illuminating light, wherein said lighting circuit means for supplying at least said D.C. base current in the period in which said shutter means is closed.

8. A light source device according to claims 6 or 7, wherein said color transmission filters transmit lights of wavelengths corresponding to red, green and blue colors.

* * * * *